US007495413B2

(12) United States Patent
Vaisnys et al.

(10) Patent No.: US 7,495,413 B2
(45) Date of Patent: Feb. 24, 2009

(54) MEDICAL DEVICE BATTERY SYSTEM INCLUDING A SECONDARY POWER SUPPLY

(75) Inventors: Gintaras A. Vaisnys, Chicago, IL (US); Giovanni C. Meier, Madison, CT (US); Glenn W. Laub, Princeton, NJ (US)

(73) Assignee: Defibtech LLC, Chicago, IL (US)

(*) Notice: Subject to any disclaimer, the term of this patent is extended or adjusted under 35 U.S.C. 154(b) by 0 days.

(21) Appl. No.: 10/453,312

(22) Filed: Jun. 3, 2003

(65) Prior Publication Data

US 2003/0205988 A1 Nov. 6, 2003

Related U.S. Application Data

(63) Continuation of application No. 09/960,859, filed on Sep. 21, 2001, now Pat. No. 6,577,102.

(51) Int. Cl.
*H02J 7/00* (2006.01)

(52) U.S. Cl. .................................................... 320/103

(58) Field of Classification Search ................. 320/103, 320/127, 128, 135, 138, 104, 105–115; 607/2, 607/29–34, 36, 5, 1

See application file for complete search history.

(56) References Cited

U.S. PATENT DOCUMENTS 4,101,787 A * 7/1978 Vail .......................... 320/138
4,106,494 A * 8/1978 McEachern ................. 600/508
4,590,943 A 5/1986 Paull et al. ..................... 607/5
4,742,831 A * 5/1988 Silvian ....................... 600/523
5,224,870 A 7/1993 Weaver et al. ............... 439/157
5,350,317 A 9/1994 Weaver et al. ............... 439/500
5,372,605 A * 12/1994 Adams et al. .................. 607/5
5,470,343 A * 11/1995 Fincke et al. ................... 607/5
5,483,165 A 1/1996 Cameron et al. ............ 324/427
5,579,234 A * 11/1996 Wiley et al. ................. 702/118
5,591,213 A 1/1997 Morgan et al. ................. 607/5
5,640,078 A 6/1997 Kou et al. ................... 320/124
5,645,571 A * 7/1997 Olson et al. .................... 607/5
5,697,955 A 12/1997 Stolte ........................... 607/5
5,700,281 A 12/1997 Brewer et al. .................. 607/5
5,721,482 A * 2/1998 Benvegar et al. ............ 320/106

(Continued)

FOREIGN PATENT DOCUMENTS

JP 2001178021 * 6/2001

OTHER PUBLICATIONS

Christopher Morris, 1992, Academic Press Dictionary of Science and Technology, Academic Press, p. 1376.*

(Continued)

*Primary Examiner*—Gary L Laxton
*Assistant Examiner*—Yalkew Fantu
(74) *Attorney, Agent, or Firm*—King & Spalding LLP

(57) ABSTRACT

A battery system for a medical device includes a first power supply and a second power supply. The first power supply is capable of being connected to the medical device to supply power to the medical device during a first operating mode of the medical device. The second power supply supplies power to at least one of a portion of the medical device and the battery system during an alternate mode, exclusive of a state the first power supply.

34 Claims, 5 Drawing Sheets

100 110 136 134 138 130 132 120 160 137 150

U.S. PATENT DOCUMENTS

| | | | | |
|---|---|---|---|---|
| 5,741,305 | A | 4/1998 | Vincent et al. | 607/5 |
| 5,749,902 | A | 5/1998 | Olson et al. | 607/5 |
| 5,773,961 | A | 6/1998 | Cameron et al. | 320/132 |
| 5,792,190 | A | 8/1998 | Olson et al. | 607/5 |
| 5,797,969 | A | 8/1998 | Olson et al. | 607/5 |
| 5,800,460 | A | 9/1998 | Powers et al. | 607/5 |
| 5,817,151 | A | 10/1998 | Olson et al. | 607/142 |
| 5,846,264 | A * | 12/1998 | Andersson et al. | 607/28 |
| D405,754 | S | 2/1999 | Barkley et al. | D13/103 |
| 5,868,790 | A | 2/1999 | Vincent et al. | 607/5 |
| 5,868,794 | A | 2/1999 | Barkley et al. | 607/5 |
| 5,879,374 | A | 3/1999 | Powers et al. | 607/5 |
| 5,889,388 | A | 3/1999 | Cameron et al. | 320/166 |
| 5,897,576 | A | 4/1999 | Olson et al. | 607/5 |
| D409,752 | S | 5/1999 | Bishay et al. | D24/187 |
| 5,904,707 | A | 5/1999 | Ochs et al. | 607/6 |
| 5,919,212 | A | 7/1999 | Olson et al. | 607/5 |
| 5,944,741 | A | 8/1999 | Ochs et al. | 607/5 |
| 5,955,956 | A | 9/1999 | Stendahl et al. | 340/635 |
| 5,964,786 | A | 10/1999 | Ochs et al. | 607/5 |
| 5,983,137 | A * | 11/1999 | Yerkovich | 607/5 |
| 5,999,493 | A | 12/1999 | Olson | 368/47 |
| 6,016,059 | A | 1/2000 | Morgan | 324/556 |
| 6,038,473 | A * | 3/2000 | Olson et al. | 607/5 |
| 6,072,299 | A | 6/2000 | Kurle et al. | 320/112 |
| 6,075,345 | A * | 6/2000 | Lee | 320/138 |
| 6,366,809 | B1 | 4/2002 | Olson et al. | 607/5 |
| 6,501,983 | B1 * | 12/2002 | Natarajan et al. | 600/517 |
| 6,546,288 | B1 * | 4/2003 | Levine | 607/28 |
| 6,577,102 | B1 * | 6/2003 | Vaisnys et al. | 320/114 |
| 6,586,850 | B1 * | 7/2003 | Powers | 307/85 |
| 6,650,942 | B2 * | 11/2003 | Howard et al. | 607/34 |
| 6,955,864 | B1 * | 10/2005 | Vaisnys et al. | 429/121 |
| 2004/0133244 | A1 * | 7/2004 | Vaisnys et al. | 607/5 |

OTHER PUBLICATIONS

Swerdlow et al., "Cardiovascular Collapse Caused by Electrocardiographically Silent 60-Hz Intracardiac Leakage Current",1999, American Heart Associationpp. 1-13.*

Machine translation of JP-2001178021.*

Heartstream®, Fore Runner® Semi-Automatic Defibrillator User's Guide, pp. 6-9 and 50, (assumed published prior to filing date).

Hewlett Packard, 43110 A Defibrillator/Monitor Operating Guide, Eighth Edition, pp. 2, 5,, 36-39, Aug. 1991.

Aligent Heartstream FR2, M3860A, M3861A, User's Guide, pp. 2-1-2-2, 2-4, 4-5, and B6, (assumed published prior to filing date).

Medtronic Physio-Control, Lifepack® 500 automated external defibrillator, Service Manual, pp. 3 of 12-4-12, 7 of 12-10 of 12, 12 of 12, (assumed published prior to filing date).

Medtronic Physio-Control, Lifepak® 500 Automated External Defibrillator Operating Instructions, pp. 2-5-2-6, 5-7-5-11, 5-16-5-17, Mar. 2001.

Survivalink FirstSave™ Operation and Service Manual, pp. 20, 29-31, 65, 70,84 and 85, 2000.

* cited by examiner 110
140
320
310
150
137
100

MEDICAL DEVICE BATTERY SYSTEM INCLUDING A SECONDARY POWER SUPPLY

RELATED APPLICATIONS

This is a continuation of Ser. No. 09/960,859, filed Sep. 21, 2001, now U.S. Pat. No. 6,557,102.

FIELD OF THE INVENTION

The present invention relates generally to battery systems, and more specifically relates to battery systems for a medical device, where the battery system includes a secondary power supply.

BACKGROUND

Many known battery-powered medical devices, such as semi-automatic external defibrillator ("AED") devices, rely on batteries to power electronics of the device, and, in the case of the AED device, to administer electric shocks to patients. For example, AED devices are used to provide electric shocks to treat patients for a variety of heart arrhythmias. The AED provides relatively high-level shocks to a patient, usually through electrodes attached to the patient's torso, to convert, for example, ventricular fibrillation to a normal sinus rhythm.

Studies have demonstrated that survival rates are high when defibrillation treatment is administered within the first few minutes following cardiac arrest. The likelihood of successful resuscitation, however, decreases by approximately 10 percent with each minute following sudden cardiac arrest. After ten minutes, very few resuscitation attempts are successful. Thus, it is advantageous to construct an AED that includes a reduced size and weight to be conveniently portable. One way to reduce the size and weight of the AED is to reduce the size and weight of the battery system.

For a defibrillation pulse to be effective in terminating cardiac arrhythmia, however, sufficient energy must reach the heart, through muscle, bone, organs and other tissues. In addition, the battery system of the AED is often called upon to power non-essential functions of the AED such as powering at least a portion of the electronics of the AED, for example, to perform AED self-tests, sound AED enunciators and visually indicate status. Thus, the battery system preferably includes enough energy to power the non-essential functions over a period of time, for example years, and still be able to deliver a high dose of energy when needed. A known solution is to include a bigger power supply in the battery system to handle these needs, which thus increases the size and cost of the AED. Another solution is to more frequently replace the power supply in the battery system, which may increase cost of operating the AED and increase the amount of maintenance that the AED requires.

Thus, there is a need for an improved battery system for a medical device such as an AED.

DETAILED DESCRIPTION

Figure 1A:
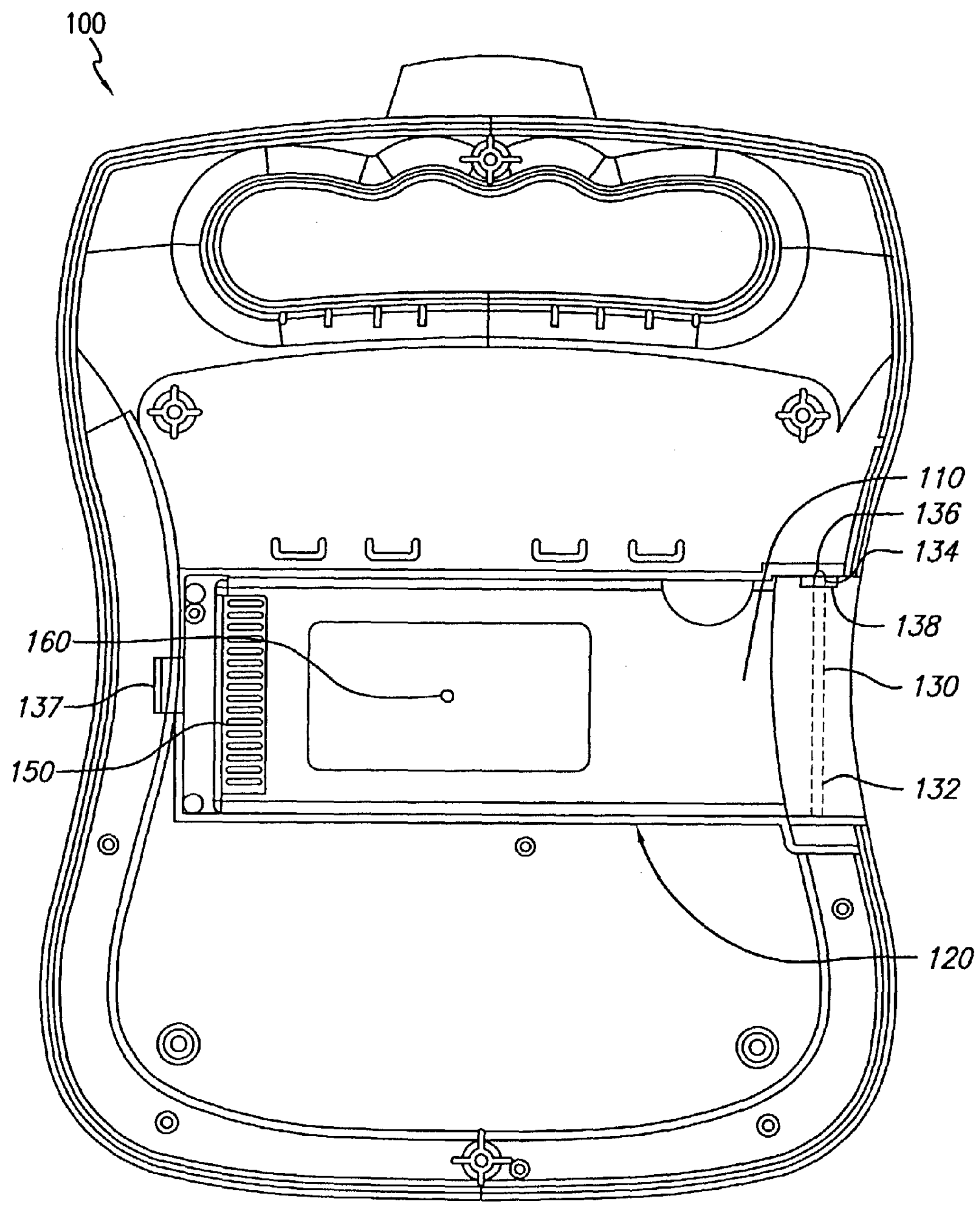
FIG. 1A illustrates a top sectional view of an AED with a battery pack installed.

FIG. 1A illustrates a top sectional view of the Semi-Automatic External Defibrillator ("AED") 100 that includes a battery system, for example battery pack 110. The AED 100 is a device to treat cardiac arrest that is capable of recognizing the presence or absence of ventricular fibrillation or rapid ventricular tachycardia or other shockable cardiac arrhythmias, and is capable of determining, without intervention by an operator, whether defibrillation should be performed. Upon determining that defibrillation should be performed, the AED automatically charges and requests delivery of electrical energy to electrodes that attach to a patient to deliver the energy to the patient's heart.

The battery pack 110 provides power to components such as electronics and a charger located in the AED 100. The charger charges a capacitor 564 (FIG. 5) of the AED 100 that provides the electrical energy to the electrodes attached to the patient. The AED 100 includes a generally rectangular shaped battery well 120 that is constructed and arranged to house the battery pack 110. The battery pack 110 is sized to slide in and out of the battery well 120 to releasably connect a power supply of the battery pack 110 to the AED 100.

Figure 1B:
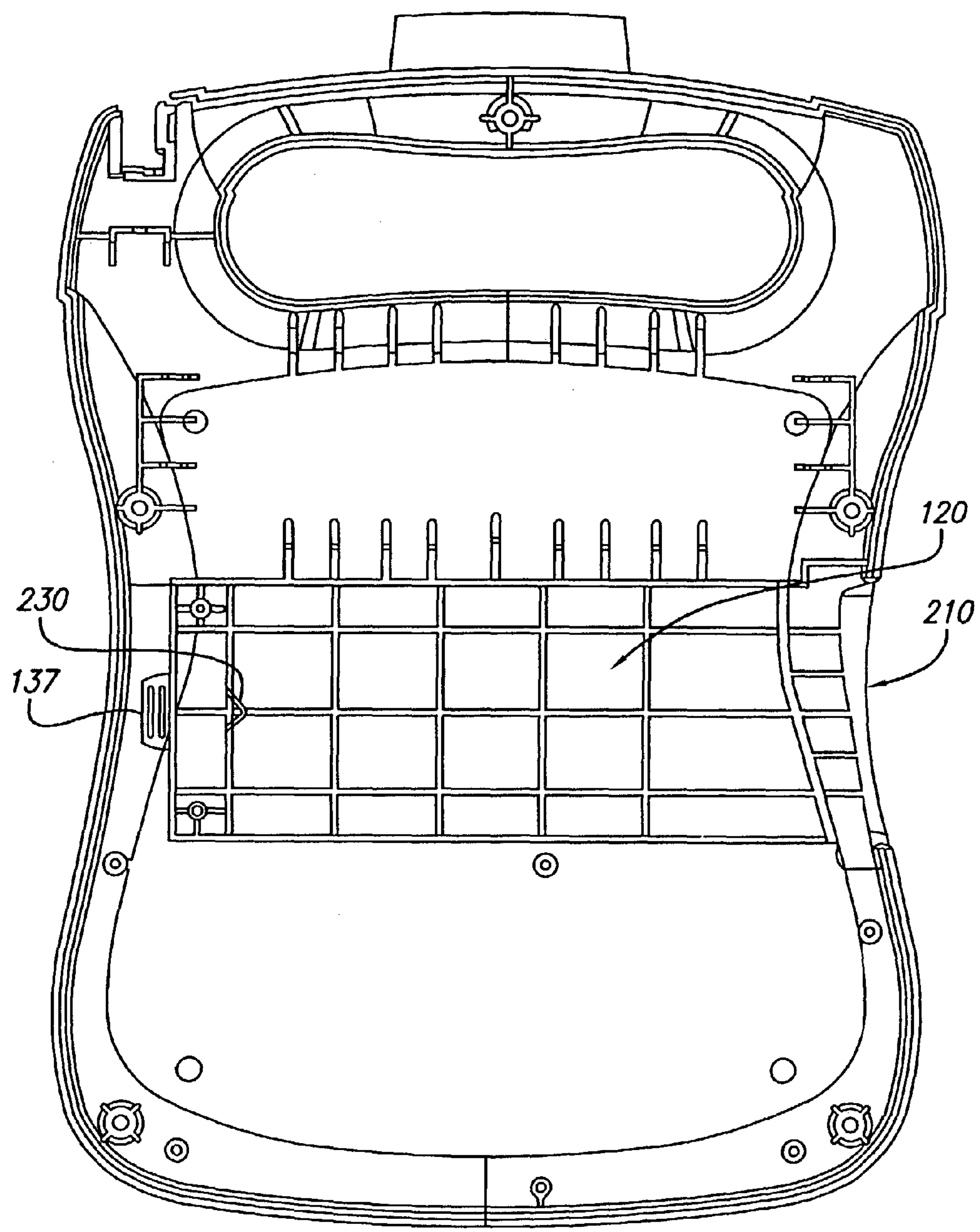
FIG. 1B illustrates a top sectional view of the AED with the battery pack removed.

FIG. 1B illustrates a top sectional view of the AED 100 and the battery well 120 with the battery pack 110 removed. An entrance 210 of the battery well 120 accommodates alignment of the battery pack 110 within the battery well 120.

Figure 2:
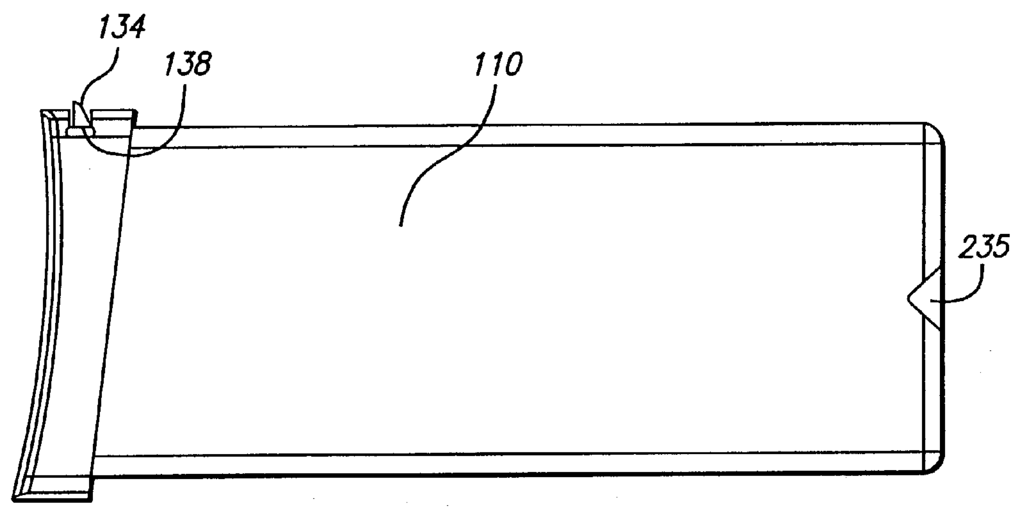
FIG. 2 illustrates a bottom view of the battery pack.

FIG. 2 illustrates a bottom view of the battery pack 110. Referring to FIGS. 1B and 2, an opposite end of the battery well 120 includes a wedge-shaped feature 230 that corresponds to a wedge-shaped receptacle 235 located in the battery pack 110. When inserting the removable battery pack 110 to the AED 100, the battery pack 110 is guided along by the battery well 120 to the wedge-shaped feature 230. The battery pack 110 is aligned at the end of its travel by the wedge shaped feature 230 in the battery well 120 via the corresponding wedge shaped receptacle 235 in the battery pack 110.

Referring to FIG. 1A, to maintain the battery pack 110 in a connected position relative to the AED 100, the battery pack 110 includes a latch 130 that retains the battery pack 110 within the battery well 120 when the battery pack is fully inserted into the battery well 120. An end of the latch 130 connects with a spring 132 to bias the latch in a normally extended position. In the normally extended position, a latching end 134 of the latch 130 extends to enter a corresponding slot 136 located in the AED 100. The latch 130 is moveable in a plane parallel to the spring 132 to compress the spring 132 to release the latching end 134 from the slot 136. When the latching end 134 is released from the slot 136, an ejection spring 137 located on the AED 100 pushes on the battery pack 110 to eject the battery pack 110 from the battery well 120. The battery pack 110 includes a slot 138 from which the latch 130 extends. Even in a fully contracted position, the latch 130 extends past the slot 138.

Figure 5:
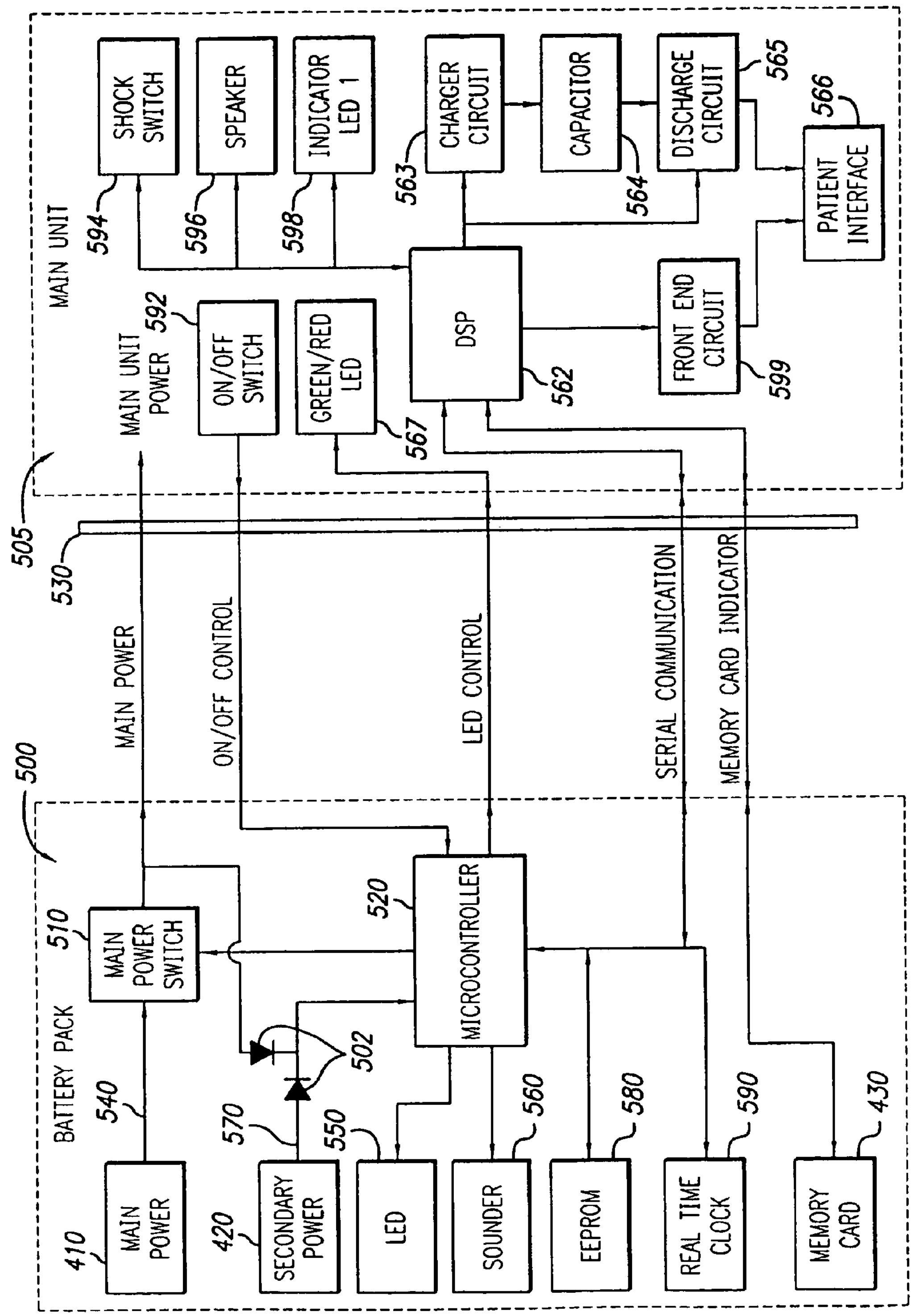
FIG. 5 illustrates a block diagram of circuitry contained with the battery pack and the AED.

The battery pack 110 also includes a printed circuit board (PCB) 140 including exposed electrical terminals 150 to connect the printed circuit board 140 to electrical circuitry contained in the AED 100, as described in more detail below. The PCB 140 includes electrical components that connect to circuitry of the AED 100 when the battery pack 110 is installed in the AED 100. The battery pack 110 includes a window 160 that is located proximate to a visual indicator, such as light emitting diode (LED) 550 (FIG. 5). The window 160 allows an operator to view the LED 550 when the battery pack 110 is removed from the AED 100. Thus, the operator can determine a status of at least one of the AED 100 and the battery pack 110 independent of the battery pack 110 being connected to the AED 100. It should be appreciated that the AED 100 could also include a window located proximate to the battery pack window 160 so that an operator can view the LED 550 when the battery pack is inserted in the AED 100.

Figure 3:
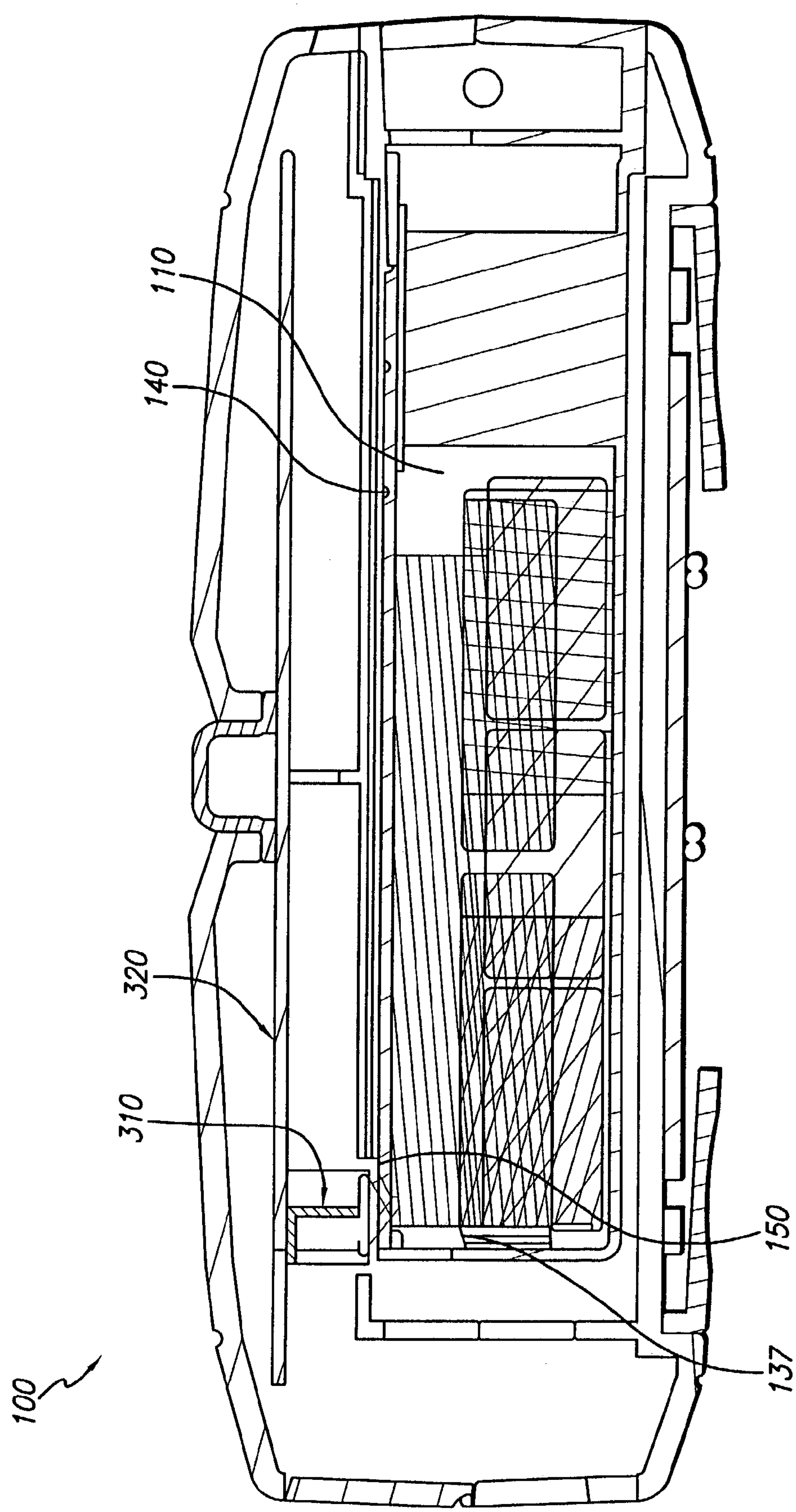
FIG. 3 illustrates a side sectional view of the AED including the battery pack.

FIG. 3 illustrates a side sectional view of the AED 100 including the battery pack 110. The electrical terminals 150 of the PCB 140 contact a connector 310 located within the AED 100, to electrically connect the battery pack PCB 140 with an AED PCB 320.

Figure 4:
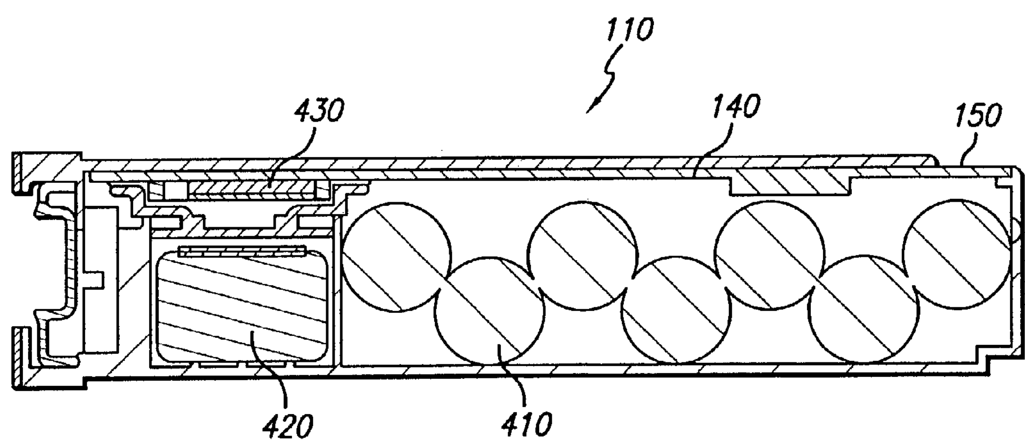
FIG. 4 illustrates a side sectional view of the battery pack including first and second battery units.

FIG. 4 illustrates a side sectional view of the battery pack 110. The battery pack 110 includes a first power supply, such as battery unit 410. The battery unit 410 powers essential power needs of the AED during a main operating mode, for example when the AED is powered on. An essential power need includes, for example, the power necessary to charge the capacitor 564 to deliver energy to the patient. The battery unit 410 is preferably not being drained of power when the AED is powered off.

The battery unit 410 includes one or more battery cells, or other power supplies, that are electrically connected together. The power supply may include other forms of energy storage, for example based on chemical or kinetic principles, such as a flywheel storage device. The battery cells can include, for example, 2/3A size batteries and/or C size batteries. The number of batteries used varies depending on a particular application but typically includes five or ten 2/3 A size batteries or four C size batteries. The five 2/3 A size batteries or four C size batteries are connected in series. Also, two sets connected in parallel of five 2/3 A batteries connected in series can be used for the battery unit 410. The battery unit 410 preferably powers electronics and a charger located in the AED 100.

The battery pack 110 also includes a secondary power supply, such as secondary battery 420. The secondary battery 420 powers at least a portion of at least one of the AED and the battery pack 110 in an alternate mode, such as when at least a portion of the AED is powered off. Those skilled in the art will appreciate that the secondary battery 420 could also be used to power the AED during other modes, such as a sleep mode or when the AED is powered on. The secondary battery 420 typically includes a single 9 Volt battery, but other power supplies could be used, such as other sized batteries or other forms of energy storage. In a preferred embodiment, the battery pack 110 accommodates replacement of the secondary battery 420. The secondary battery 420 can be sized smaller than the battery unit 410 and contain energy sufficient to power, for example, electric circuitry of the AED 100 and the battery PCB 140.

The secondary battery 420 can be used to power circuitry exclusive of a state of the battery unit 410 and without draining power from the battery unit. Diodes 502 (FIG. 5) electrically isolate the battery unit 410 from the secondary battery 420. Electric circuitry of the battery pack PCB 140 is described in more detail below with regard to FIG. 5. Such circuitry includes a socket to removably receive a memory device (FIG. 4), such as a memory card 430 or a multi-media card (MMC).

When the AED 100 is powered on and attached to the patient, the memory card 430 records the patient's electrocardiogram (ECG) signals, audio signals received from a microphone located on the AED 100, and other operational information such as results of an analysis done on the patient by software of the AED 100. The memory card 430 may also hold files that may be used to upgrade the software of the AED 100 or to provide user training mode software for the AED.

FIG. 5 shows a block diagram illustrating battery pack circuitry 500 contained with the battery pack 110, for example, on the battery pack PCB 140, and main unit circuitry 505. The circuitry 500 includes a main power switch 510. The main power switch 510 connects with a digital logic, such as micro-controller 520, that turns the main power switch 510 on and off and controls other circuitry 500 of the battery pack PCB 140. In addition to or in place of the micro-controller 520, the digital logic can also include a microprocessor, a programmable logic device (PLD), a gate array and a custom integrated circuit. Other digital logic could also be used such as a Programmable Interface Controller (PIC) manufactured by Microchip Technologies, located in Chandler, Ariz.

The micro-controller 520 connects with a main AED connector 530 that connects circuitry of the battery pack PCB 140 to circuitry of the AED 100. When the operator engages a power switch 592 located on the AED 100, the micro-controller 520 receives a signal from the main unit connector 530 indicating that the power switch has been engaged. Thereafter, the micro-controller 520 enables the main power switch 510 to provide an electrical power between the battery unit 410 of battery pack 110 and the electronics of the AED 100. The battery pack PCB 140 also includes a main battery connector 540 to connect the battery unit 410 to the main unit connector 530 and other circuitry of the battery pack PCB 140.

The micro-controller 520 also controls a visual indicator, such as LED 550 and an audio indicator, such as sounder 560 that are used to automatically communicate information to the operator. For example, when the AED 100 fails a self-test, the operator is notified by a chirping sound from the sounder 560. Moreover, the LED 550 blinks green to indicate that a status of components of the AED 100 is within an acceptable operating range. Those skilled in the art can appreciate the opposite could be true, i.e., that a blinking light indicates a fault condition. According to a preferred embodiment, if the LED 550 is not blinking an error exists, for example, in the circuitry 500, or the battery unit 410 or secondary battery 420 are depleted. The micro-controller 520 monitors a signal of a comparator connected to secondary battery 420 to monitor a status of the secondary battery 420, for example, to determine whether or not power of the secondary battery 420 is low or depleted.

Regarding the main unit circuitry 505, a digital signal processor (DSP) 562 processes instructions and data of the AED 100. The DSP 562 connects with a charger circuit 563 and discharger circuit 565 to control the charging and discharging of main unit capacitor 564. The capacitor charger 563 connects the battery unit 410 to the capacitor 564. The capacitor 564 connects to a discharge circuit 565 that connects to patient interface 566 to deliver shocks to the patient.

The micro-controller 520 also controls a red and green LED 567, or a red LED and a green LED, located on the AED 100. The micro-controller 520 connects to the red and green LED 567, for example, via pins of the main unit connector 530. The micro-controller 520 causes the LED 567 to blink green when the AED 100 is operating properly and causes the LED 567 to blink red when components of the AED are not within the acceptable operating range, for example, a component of the AED 100 failed during a self-test procedure. If the LED 567 is not blinking when the battery pack 110 is installed into the AED 100, components of the AED 100 and the battery pack 110 should be checked. The battery pack LED 550 is preferably disabled when the battery pack 110 is installed.

The secondary battery 420 powers the micro-controller 520, the LED 550 and the LED 567, which helps to maintain the integrity of the battery unit 410 that provides power to electronics and the capacitor charger located in the AED 100. A secondary battery connector 570 connects the secondary battery 420 to the circuitry of the battery pack PCB 140.

The battery pack circuitry 500 also includes an electrically erasable programmable read only memory (EEPROM) 580 connected to the micro-controller 520 and the main unit connector 530. The EEPROM 580 stores information that may be relevant to an owner, service person or operator of the AED 100. The EEPROM 580 stores information regarding, for example, the number of shocks the battery unit 410 has been used for, that the AED 100 has been activated, the date of manufacture of the battery pack 110 and status information regarding a status of components of the battery pack 110 and the AED 100. The DSP 562 of the AED 100 connects to a bus that connects to a real time clock (RTC) 590, the EEPROM 580 and the micro-controller 520. Typically once per power up of the AED 100, the DSP accesses the RTC 590 to set a main unit clock of the AED 100 that is located in the DSP.

The main unit circuitry 505 also includes a switch 592, such as an ON/OFF switch, that connects to the micro-controller 520 via the main unit connector 530. A shock switch 594 connects to the DSP 562 to allow an operator to administer a shock to the patient. A speaker 596 and indicator LEDs 598 connect to the DSP 562 to supply instructions or other information to the operator. Front end circuitry 599 connects between the DSP 562 and the patient interface 566 to process and/or provide the DSP 562 with information from the patient.

While the invention has been described above by reference to various embodiments, it will be understood that many changes and modifications can be made without departing from the scope of the invention. It is therefore intended that the foregoing-detailed description be understood as an illustration of the presently preferred embodiments of the invention, and not as a definition of the invention. It is only the following claims, including all equivalents, which are intended to define the scope of this invention.

We claim:

1. A power supply system for an external defibrillator having an operating mode and an alternate mode, the power supply system comprising:

an external defibrillator having a main unit circuit and a battery pack circuit, the main unit circuit and battery pack circuit cooperating to deliver energy to a patient and the battery pack circuit for providing functions of the external defibrillator other than delivering energy to the patient, a first power supply comprising a first battery, the first power supply providing electrical power to the main unit circuit and the battery pack circuit;

a main power switch interposed between the first power supply and both of the main unit circuit and the battery pack circuit, the main power switch having a first state and a second state, the main power switch in the first state allowing the electrical power to flow from the first power supply to the main unit circuit and the battery pack circuit during the operating mode and in the second state preventing the electrical power from flowing from the first power supply to the main unit circuit and the battery pack circuit during the alternate mode, the main power switch alternatable between the first and second states; and a second power supply comprising a second battery, the second power supply and the first power supply being connected by circuitry, the circuitry and main power switch cooperating such that when the main power switch is in the second state, the second power supply provides electrical power to the battery pack circuit and the circuitry isolates the second power supply from the main unit circuit, and when the main power switch is in the first state, the circuitry isolates the second power supply from the battery pack circuit and the main unit circuit.

2. The power supply system of claim 1 wherein the battery pack circuit comprises circuitry reporting a status of the external defibrillator.

3. The power supply system of claim 1 wherein the battery pack circuit comprises circuitry sounding an enunciator.

4. The power supply system of claim 1 wherein the battery pack circuit comprises circuitry running a self-test routine.

5. The power supply system of claim 1 wherein the battery pack circuit includes a memory device.

6. The power supply system of claim 1 wherein the battery pack circuit comprises a microcontroller.

7. The power supply system of claim 1 wherein the battery pack circuit includes electronically erasable programmable read only memory.

8. The power supply system of claim 1 wherein the battery pack circuit comprises at least one visual indicator.

9. The power supply system of claim 8 wherein the visual indicator comprises a light emitting diode.

10. The power supply system of claim 1 wherein the second power supply is replaceable.

11. The power supply system of claim 1 wherein the first battery comprises a plurality of battery cells.

12. The power supply system of claim 1 wherein the power supply system is capable of being removed from the external defibrillator.

13. A method of powering components of an external defibrillator having an operating mode and an alternate mode, the external defibrillator having a main unit circuitry and a battery pack circuitry which cooperate for delivering energy to a patient during the operating mode, and the battery pack circuitry for powering functions of the external defibrillator other than delivering energy to a patient during the alternate mode, the second power supply and the first power supply being connected to intermediate circuitry, the method comprising:

controlling power from a first power supply with a main power switch, the first power supply comprising a first battery, the main power switch interposed between the first power supply and both of the main unit circuitry and the battery pack circuitry, the main power switch having a first state and a second state, the main power switch alternatable between the first and second states;

allowing the electrical power to flow from the first power supply to the main unit circuit and the battery pack circuitry during the operating mode when the main power switch in the first state and while the intermediate circuitry isolates the second power supply from the battery pack circuit;

preventing the electrical power from flowing from the first power supply to the main unit circuit and the battery pack circuitry during the alternate mode when the main power switch is in the second state; and powering the battery pack circuitry of the external defibrillator with a second power supply comprising a second battery when the intermediate circuitry isolates the second power supply from the main unit circuitry and while the main power switch is in the second state.

14. The method of claim 13 wherein the battery pack circuitry comprises circuitry reporting a status of the external defibrillator.

15. The method of claim 13 wherein the battery pack circuitry comprises circuitry sounding an enunciator.

16. The method of claim 13 wherein the battery pack circuitry comprises circuitry running a self-test routine.

17. The method of claim 13 wherein the battery pack circuitry includes a memory device.

18. The method of claim 13 wherein the battery pack circuitry comprises a microcontroller.

19. The method of claim 13 wherein the battery pack circuitry includes electronically erasable programmable read only memory.

20. The method of claim 13 wherein the battery pack circuitry comprises at least one visual indicator.

21. The method of claim 20 wherein the visual indicator comprises a light emitting diode.

22. The method of claim 13 wherein the second battery is replaceable.

23. The method of claim 13 wherein the first battery comprises a plurality of power cells.

24. The method of claim 13 wherein the first battery and the second battery form a battery system that is capable of being removed from the external defibrillator.

25. In an external defibrillator having energy delivery circuitry for delivering energy to a patient and battery pack circuitry controlling functions of the external defibrillator other than delivering energy to a patient, the improvement comprising:

a battery system for the external defibrillator having a first power supply comprising a first battery and a second power supply comprising a second battery, the first power supply being connected to the energy delivery circuitry by a main power switch, the main power switch interposed between the first power supply and both of the energy delivery circuitry and the battery pack circuitry, the main power switch in the first state allowing the electrical power to flow from the first power supply to the energy delivery circuitry and the battery pack circuitry during an operating mode, and in the second state preventing the electrical power from flowing from the first power supply to the energy delivery circuitry and the battery pack circuitry during an alternate mode, the main power switch alternatable between the first and second states, the second power supply and the first power supply being connected by intermediate circuitry, the intermediate circuitry and main power switch cooperating such that when the main power switch is in the second state, the second power supply provides electrical power to the battery pack circuitry and the intermediate circuitry isolates the second power supply from the main unit circuit, and when the main power switch is in the first state, the intermediate circuitry isolates the second power supply from the battery pack circuitry and the energy delivery circuitry.

26. The external defibrillator of claim 25 wherein the battery pack circuitry comprises a microcontroller.

27. The external defibrillator of claim 25 wherein the first battery comprises a plurality of power cells.

28. The external defibrillator of claim 25 wherein the battery system is removable from the external defibrillator.

29. The power supply system of claim 1 wherein the battery pack circuit comprises digital logic connected between the main power switch and the main circuit for controlling the main power switch between its first and second states.

30. The power supply system of claim 1 wherein the first power supply has a voltage greater than the second power supply.

31. The power supply system of claim 30 wherein the circuitry comprises a first diode positioned between the second power supply and both of the main unit circuit and the battery circuit, the first diode isolates the second power supply from the main unit circuit while allowing the second power supply to provide electrical power to the battery circuit when the main power switch is in the second state.

32. The power supply system of claim 31 wherein the circuitry comprises a second diode positioned between the second power supply and both of the main unit circuit and the battery circuit, the second diode isolates the second power supply from the battery pack circuit and the main unit circuit when the main power switch is in the first state.

33. The method of claim 13 wherein the intermediate circuitry comprises first and second diodes.

34. The external defibrillator of claim 25 wherein the intermediate circuitry comprises first and second diodes.

* * * * *